United States Patent [19]

Castaldi et al.

[11] Patent Number: 4,937,367
[45] Date of Patent: Jun. 26, 1990

[54] PROCESS FOR THE PREPARATION OF INTERMEDIATES FOR THE SYNTHESIS OF FOSFOMYCIN

[75] Inventors: Graziano Castaldi, Briona; Claudio Giordano, Monza, both of Italy

[73] Assignee: Zambon Group S.p.A., Vicenza, Italy

[21] Appl. No.: 217,976

[22] Filed: Jul. 12, 1988

[30] Foreign Application Priority Data

Jul. 15, 1987 [IT] Italy ................. 21303 A/87
Dec. 21, 1987 [IT] Italy ................. 23125 A/87

[51] Int. Cl.$^5$ ............................................. C07C 143/68
[52] U.S. Cl. ........................................ 558/45; 558/143
[58] Field of Search ............... 260/502.4 R; 558/143, 558/45; 549/217

[56] References Cited

U.S. PATENT DOCUMENTS 3,657,282  4/1972  Christensen et al. .............. 558/45
3,819,676  6/1974  Christensen et al. .............. 558/45

FOREIGN PATENT DOCUMENTS 1266611  3/1972  United Kingdom .

OTHER PUBLICATIONS

Clin et al., Bull. Soc. Pharmacie de Bordeau, vol. 121, No. 1-2, pp. 3-11 (1982).
Chem. Pharm. Bull. Ohzeki et al. Stereochemical Studies, ILVIII, vol. 25, pp. 2676-2680 (1977).
Hydrolysis by a-Chymotrypsin, Cohen et al., Inversion of Stereospecificity in Hydrolysis by a-chymotrypsin, pp. 1685-1691 (1963).

*Primary Examiner*—Nicky Chan
*Attorney, Agent, or Firm*—Stevens, Davis, Miller & Mosher

[57] ABSTRACT

A process is described for the preparation of intermediates useful in the synthesis of Fosfomycin.

More particularly, an enantioselective process is described for the preparation of derivatives of (1S,2S)-1,2-dihydroxypropyl-phosphonic acid of formula

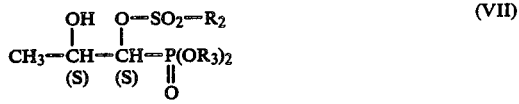

wherein $R_2$ and $R_3$ have the meanings reported in the specification.

5 Claims, No Drawings

PROCESS FOR THE PREPARATION OF INTERMEDIATES FOR THE SYNTHESIS OF FOSFOMYCIN

The present invention concerns a process for the preparation of intermediates useful in the synthesis of Fosfomycin and more particularly it concerns an enantioselective process for the preparation of derivatives of 1,2-dihydroxypropyl-phosphonic acid. By the name Fosfomycin (Merck Index, 10th Ed., 4137, page 607) is indicated the (1R,2S)-cis-diastereoisomer of 1,2-epoxypropylphosphonic acid of formula

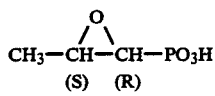
(I)

The compound, firstly isolated in some species of Streptomyces, showed to be useful, either as such or as a salt thereof, as anti-bacterial agent in human therapy being able to inhibit the growth of gram-positive and gram-negative pathogenic agents.

Presently Fosfomycin is made available by chemical synthesis.

The widely used procedure comprises the preparation by several steps, of cis-1-propenyl-phosphonic acid and its epoxidation optionally via the intermediate formation of a halohydrin.

Thereby an enantiomeric mixture of (1S,2R) and (1R,2S)-cis-1,2-epoxypropyl-phosphonic acid is obtained.

The enantiomer (1R,2S) must be then separated by salt formation with an optically active base.

The optically active amine must then be recovered and recycled while the undesired enantiomer is lost.

It would be very important to have available an easy and inexpensive method for transforming the enantiomer 1S,2R of the cis-1,2-epoxypropyl-phosphonic acid into the desired enantiomer by interconversion and not by the formation of an enantiomeric mixture to be resolved. Otherwise, as an alternative it would be very important to have available a diastereoselective process for the preparation of (1R,2S)-1,2-epoxypropyl-phosphonic acid, i.e. Fosfomycin.

A convenient approach could be the epoxidation of a suitable (1S,2S)-1,2-dihydroxypropyl-phosphonic acid derivative.

Therefore, in order to avoid a resolution procedure with the expensive steps therein involved, a possibility is that of having available a process for the preparation of a (1S,2S)-1,2-dihydroxypropyl-phosphonic acid derivative which might be easily transformed into Fosfomycin.

The realization of said diastereoselective process might use, as a starting material, a chiral building block (chiron) having three carbon atoms, at least one of which in the right configuration. A suitable chiral building block is 2(S)-hydroxy-propionic acid, i.e. the natural occuring inexpensive lactic acid.

Belgian Patent No. 733,058 (Merck & Co. Inc.) uses lactic acid as a starting material for the preparation of Fosfomycin.

However, the specific intermediates and the reaction conditions therein described do not result in a diastereoselective process. Due to several steps involving substantial side-reactions and other drawbacks, the process described in the above cited Belgian Patent may be suitable only for the preparation of mixtures of the four possible stereoisomers of 1,2-epoxypropyl-phosphonic acid. We have now found, and this is the object of the present invention, an enantioselective process for the preparation of (1S,2S)-1,2-dihydroxypropyl-phosphonic acid derivatives useful as intermediates for the synthesis of Fosfomycin.

The process we have found allows also the transformation of the (1S,2R) isomer of cis-1,2-epoxypropyl-phosphonic acid (the undesired enantiomer) into Fosfomycin. Thus, at the same time, the process we have found makes available two very useful alternatives in the synthesis of Fosfomycin.

The (1S,2S)-1,2-dihydroxypropyl-phosphonic acid derivatives obtained by the process object of the invention, have the following formula

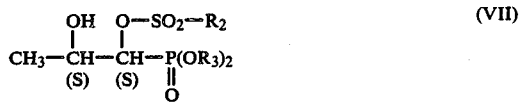
(VII)

wherein
$R_2$ represents lower alkyl, aryl or alkylaryl having up to 12 carbon atoms,
the substituents $R_3$, independently, represent hydrogen or sodium, lower alkyl or benzyl.

The compounds of formula VII are new and are a further object of the present invention.

Scheme 1 herebelow shows the steps of the process which, in the following, will be explained and discussed in details.

Scheme 1

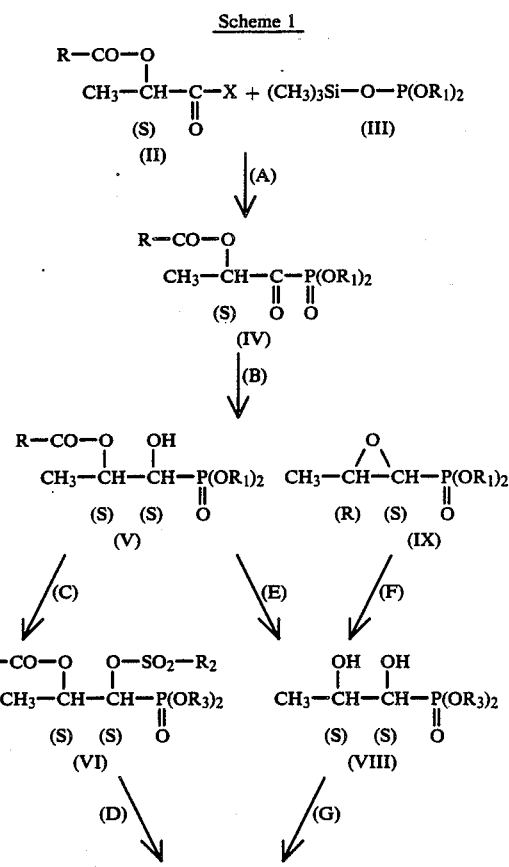

-continued
Scheme 1

$$\begin{array}{c} \text{OH} \quad \text{O}-\text{SO}_2-\text{R}_2 \\ | \quad \quad | \\ \text{CH}_3-\text{CH}-\text{CH}-\text{P(OR}_3)_2 \\ \text{(S)} \quad \text{(S)} \quad \overset{\|}{\text{O}} \end{array} \quad \text{(VII)}$$

The steps reported in Scheme 1 are the following:

(A) the reaction of an O-acylated derivatives of lactic acid of formula $$\begin{array}{c} \text{R}-\text{CO}-\text{O} \\ | \\ \text{CH}_3-\text{CH}-\text{C}-\text{X} \\ \text{(S)} \quad \overset{\|}{\text{O}} \end{array} \quad \text{(II)}$$

wherein
R is lower alkyl, lower alkoxy, an optionally substituted phenyl, benzyl or naphthyl;
X is a chlorine or bromine atom, lower alkoxy, lower alkylsulphonyloxy or lower alkoxycarbonyloxy;
with a trimethylsilyl-phosphite of formula $$(\text{CH}_3)_3\text{Si-O-P(OR}_1)_2 \quad \text{(III)}$$

wherein the $R_1$s, equal to or different from each other, represent lower alkyl, benzyl or trimethylsilyl, affords a propionyl-phosphonate of formula $$\begin{array}{c} \text{R}-\text{CO}-\text{O} \\ | \\ \text{CH}_3-\text{CH}-\text{C}-\text{P(OR}_1)_2 \\ \text{(S)} \quad \overset{\|}{\text{O}} \quad \overset{\|}{\text{O}} \end{array} \quad \text{(IV)}$$

wherein R and $R_1$ have the above reported meanings;

(B) the reduction of compound IV by a borohydride or an aluminum-hydride in an aprotic solvent affords the compound of formula $$\begin{array}{c} \text{R}-\text{CO}-\text{O} \quad \text{OH} \\ | \quad \quad | \\ \text{CH}_3-\text{CH}-\text{CH}-\text{P(OR}_1)_2 \\ \text{(S)} \quad \text{(S)} \quad \overset{\|}{\text{O}} \end{array} \quad \text{(V)}$$

wherein R and $R_1$ have the above reported meanings.

When substituents $R_1$ represent trimethylsilyl radicals, these can be removed according to conventional techniques (for example by treatment both with acids and bases) in the most appropriate step of the process, preferably at the stage of compound IV or after having performed its reduction to compound V, thereby obtaining the corresponding free phosphonic acids or sodium salts.

(C) the reaction of compound V with a halide or other reactive derivative of a sulphonic acid, in an inert solvent optionally in the presence of a base, affords the compound of formula $$\begin{array}{c} \text{R}-\text{CO}-\text{O} \quad \text{O}-\text{SO}_2-\text{R}_2 \\ | \quad \quad | \\ \text{CH}_3-\text{CH}-\text{CH}-\text{P(OR}_3)_2 \\ \text{(S)} \quad \text{(S)} \quad \overset{\|}{\text{O}} \end{array} \quad \text{(VI)}$$

wherein R has the above reported meanings, $R_2$ is lower alkyl, aryl or alkylaryl up to 12 carbon atoms, D or L camphoryl; the $R_3$s, equal or different from each other, represent hydrogen or sodium atoms, lower alkyl or benzyl;

(D) the deprotection of the hydroxy group in position 2 of compound VI by reaction with water or an alcohol in the presence of a strong acid affords the (1S,2S)-1,2-dihydroxypropyl-phosphonic acid derivative of formula $$\begin{array}{c} \text{OH} \quad \text{O}-\text{SO}_2-\text{R}_2 \\ | \quad \quad | \\ \text{CH}_3-\text{CH}-\text{CH}-\text{P(OR}_3)_2 \\ \text{(S)} \quad \text{(S)} \quad \overset{\|}{\text{O}} \end{array} \quad \text{(VII)}$$

wherein $R_2$ and $R_3$ have the above reported meanings.

(E) The deprotection of the hydroxy group in position 2 of compound V carried out in water or in alcohol in the presence of a strong acid affords the (1S,2S)-1,2-dihydroxypropyl-phosphonic acid derivatives of formula $$\begin{array}{c} \text{OH} \quad \text{OH} \\ | \quad \quad | \\ \text{CH}_3-\text{CH}-\text{CH}-\text{P(OR}_3)_2 \\ \text{(S)} \quad \text{(S)} \quad \overset{\|}{\text{O}} \end{array} \quad \text{(VIII)}$$

wherein the $R_3$s have the above reported meanings; the reaction conditions can be identical to those of step D.

(F) Compound VIII may also be obtained by treatment of (1S,2R)-cis-1,2-epoxypropyl-phosphonic acid esters with water. The reaction of step F allows, through the reaction of step G, the conversion of the undesired enantiomer into Fosfomycin.

(G) The reaction of compound VIII with a reactive derivative (e.g. halide) of an arylsulphonic acid affords the compounds of formula VII in which $R_2$ is an aryl or alkylaryl up to 12 carbon atoms.

In substituents X, R, $R_1$, $R_2$ and $R_3$ the expression lower alkyl means a linear or branched alkyl radical having from 1 to 4 carbon atoms, specific examples are methyl, ethyl, propyl, isopropyl, butyl, tert.butyl; lower alkoxy means a linear or branched alkoxy radical having from 1 to 4 carbon atoms, specific examples are methoxy, ethoxy, tert.butoxy; the optional substituents of the phenyl, benzyl or naphthyl group in the meanings of R, comprise from 1 to 3 substituents selected from the group consisting of halogen atoms, lower alkyl, lower alkoxy and nitro, specific examples include 4-chlorophenyl, 4-chlorobenzyl, 2,6-dichlorophenyl, 4-methoxyphenyl, 4-methoxybenzyl, 4-nitrophenyl, 2,4-dinitrophenyl, 4-isobutylphenyl, 2,4,6-trimethylphenyl, 4-methylbenzyl.

In the meanings of $R_2$, the expression aryl or alkylaryl up to 12 carbon atoms indicates an aromatic group selected among phenyl or naphthyl which can be substituted by alkyl groups, the total number of carbon atoms being 12; specific examples are phenyl, tolyl, 4-ethylphenyl, 2,4,6-trimethylphenyl, 2-naphthyl and 1-naphthyl.

It is self evident that other alkyl or alkoxy radicals having a number of carbon atoms higher than 4 may be equally suitable in as much as they do not participate to the reactions above described. Similarly, the meanings of $R_2$ have been limited to those corresponding to the most common sulphonic acids but other sulphonic acids are equally suitable.

The steps forming the process object of the invention will be in the following discussed and, where appropriate, will be compared with similar steps described in Belgian Patent No. 733,058.

STEP A

Most of the compounds of formula II are known compounds. For example 2(S)-acetoxy-propionic acid is described in J. Am. Chem. Soc., 85, 1685, (1963) and its acyl chloride (II, R=CH3) is described in Chem. Pharm. Bull., 25, 2676, (1977).

Several procedures are used for the preparation of the compounds of formula II; one of these comprises the reaction of lactic acid with the suitable acyl chloride (e.g., acetylchloride, propionyl chloride, methylchloroformate, ethyl-chloroformate) in the presence of a tertiary amine (e.g. N-methyl-morpholine, triethylamine, etc.), alternatively the reaction may be carried out by reacting lactic acid with the appropriate carboxylic acid in the presence of a mineral acid (e.g. sulphuric acid).

The preparation of the acyl chlorides of formula II may be carried out by conventional procedures starting from 2(S)-acyloxy lactic acid, e.g. by reaction with thionyl or oxalyl chloride optionally in the presence of an inert solvent.

The other compounds of formula II may be prepared from lactic acid or its 2-O-acylated derivatives by reaction with an alkylsulphonyl chloride or a chlorocarbonate in an inert solvent and optionally in the presence of a tertiary amine. The compounds of formula II in which X is an alkoxy group may be prepared by 2-O-acylation of an ester of lactic acid.

The first step of the process consists in the reaction of a compound of formula II with a trimethylsilyl-dialkylphosphite of formula III.

The reaction may be carried out without any solvent or catalyst and also at room temperature.

The reactants are used in a substantially equimolecular amount and, at the end of the reaction (usually after 1-2 hours), the formed trimethylsilyl derivative (e.g. chloride) is separated at reduced pressure or by other suitable methods and the corresponding compound IV is obtained in substantially quantitative yield.

An alternative procedure of particular industrial interest, consists in the preparation in situ of the compounds of formula III. In this case a silylating agent and a dialkylphosphite are charged in the reactor optionally in the presence of a tertiary amine and an inert solvent, and finally the compound of formula II is slowly added.

Suitable silylating agents include trimethylsilyl chloride, N,N-di-trimethylsilyl-urea, N-trimethylsilyl-imidazole, trimethylsilyl-ethers such as hexamethyldisiloxane and trimethylsilyl-amines such as trimethylsilyl-diethylamine and hexamethyldisilazane, in this latter cases no tertiary amine is required.

The above cited Belgian patent describes the reaction of a derivative of lactic acid which may be represented by the formula:

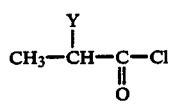

(II-A)

wherein Y is, inter alia, an alkyl- or arylsulphonyloxy radical, a halogen atom, an alkenyloxy, alkynyloxy or benzyloxy radical, with a phosphite triester of formula P(OR')3 (wherein R' has various meanings such as alkyl, aralkyl, aryl, heteroaryl, alkenyl or alkynyl).

The reaction is carried out by adding the reactants to an inert solvent at room temperature and then by heating the reaction mixture up to the boiling temperature of the solvent.

However, we have found that, when the substituent Y is a good leaving group, the main reaction product is not a propionylphosphonate but it is an olefin of formula

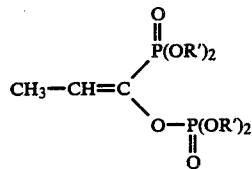

STEP B

It consists in the reduction of the carbonyl in the compound of formula IV obtained by step A.

The reduction is carried out in an aprotic solvent using a borohydride or an aluminumhydride as reducing agent.

Examples of suitable aprotic solvents are toluene, tetrahydrofuran, benzene, diethylether, methylenechloride.

Preferred borohydrides are sodium borohydride and tetraalkylammonium borohydrides (e.g. tetrabutylammonium borohydride); other useful borohydrides include sodium mono, di or triacyloxy borohydrides such as triacetoxyborohydride, sodium cyanoborohydride, zinc borohydride, lithium borohydride, lithium triethylborohydride, tris-sec.butylborohydride salts such as L or K-selectride, complexes of sodium borohydride with polyethylenglicols.

Suitable aluminumhydrides include lithium aluminumhydride, lithium diisobutylaluminumhydride and sodium di-(2-methoxyethoxy)-aluminumhydride.

By a practical point of view it is also very important the use of sodium borohydride supported on silica or alumina.

Of a particular industrial interest is also the use of a stoichiometric amount of sodium borohydride associated with a catalytic amount (1-20% by weight with respect to the borohydride) of an agent suitable for increasing the solubility in the aprotic solvent in which the reaction occurs.

Agents suitable for increasing the solubility are salts of tetraalkylammonium or phosphonium, crown ethers, trialkylborates (e.g. trimethylborate) and dipolar aprotic solvents compatible with the borohydride such as dioxane, dimethylformamide and dimethylsulphoxide in admixture with tetramethylenesulphone.

The reaction, carried out at a temperature comprised between −80° C. and room temperature, provides with high diastereoselectivity the compound of formula V with 1S,2S configuration. In many cases the diastereomeric ratio V(1S,2S):V(1R,2S) is higher than 90:10.

Generally, crystallization of the crude or column chromatography provides the desired compound V (1S,2S) in pure form. In the above cited Belgian patent, the reduction of compounds depicted as follows:

$$\underset{\underset{O}{\overset{\overset{Y}{|}}{CH_3-CH-\overset{\|}{C}-\overset{\|}{P}(OR')_2}}}{} \quad \text{(IV-A)}$$

$$CH_3-CH=C\overset{OSO_2R_2}{\underset{\underset{O}{\overset{\|}{P}(OR_1)_2}}{\diagdown}}$$

is reported too.

According to the reaction conditions therein cited the reduction of compounds IV-A may be carried out, inter alia, by sodium borohydride in methanol or ethanol.

However, we have found that when the reduction of compounds of formula IV-A (in which Y is benzyloxy) is carried out in methanol according to the reaction conditions therein described by using industrially available sodium borohydride which usually has a rather basic nature, undesired side reactions may start which provide as main product (up to 80%) esters of 2-benzyloxy-propionic acid which derive from the cleavage of the carbon-phosphorous bond.

A corresponding by-product deriving from the cleavage of the C-P bond is obtained in relevant amounts also when in the compounds of formula IV-A, Y is a methanesulphonyloxy group.

Moreover, in the obtained reaction product the diastereoselectivity appears to be rather low.

On the contrary, in the reaction conditions we describe the possible basicity of sodium borohydride does not have a detectable influence and the reduction product is obtained with high diastereoselectivity.

STEP C

The reaction of step C is a per se known reaction consisting in the acylation with a sulphonic acid of the hydroxy group in position 1 of the compounds of formula V obtained by step B.

The chloride of the sulphonic acid, e.g. methanesulphonic acid, ethanesulphonic acid, benzenesulphonic acid, p.toluenesulphonic acid, 1 or 2-naphthylsulphonic, D or L-camphorsulphonic acid, is reacted with compound V in an inert solvent such as benzene, toluene, xylene, methylenchloride, diethylether and optionally in the presence of a tertiary amine.

STEP D

It consists in the deprotection of the hydroxy group in position 2. The reaction is conveniently carried out by solvolysis in water or in an alcohol (e.g. methanol or ethanol) in the presence of a catalytic amount of a strong acid such as sulphuric acid, methanesulphonic acid, p.toluenesulphonic acid.

Depending on the reaction conditions and solvent and by the workup conditions, the reaction may afford the compounds of formula VII in which $R_3$ has the same meaning as $R_1$ or the compounds of formula VII in which $R_3$ is a hydrogen atom. These latter derive from the hydrolysis of the phosphonic esters.

This step is particularly important. In fact we have found that, if a compound of formula VI is subjected to epoxidation reaction according to what herein after discussed, beside Fosfomycin a relevant amount of an undesired by-product is obtained.

The by-product, which, depending on the meanings of R, may be the main reaction product (up to 90%) is an olefin of formula wherein $R_1$ ed $R_2$ have the above reported meanings.

STEP E

This step is carried out according to the same reaction conditions of step D.

Also in this case, the specific meanings of $R_3$ in the obtained compound of formula VIII will depend on the meanings of $R_1$ in the starting compound of formula V and on the reaction and work-up conditions.

STEP F

A particularly important further aspect of the present invention consists in the fact that the compound of formula VIII can be prepared by opening the epoxy ring of esters of (1S,2R)-cis-1,2-epoxypropyl-phosphonic acid.

Since this acid is the undesired isomer that is obtained by known processes for the synthesis of Fosfomycin, it results that the process object of the present invention represents also a method for transforming into the right enantiomer the undesired enantiomer that is obtained by the normal processes of industrial synthesis of Fosfomycin and that normally is discarded.

According to this aspect of the invention the esters of the (1S,2R)-cis-1,2-epoxypropyl-phosphonic acid are transformed by treatment with water under heating into the esters of formula VIII and these by reaction with a reactive derivatives of an arylsulphonic acid (step G) in conformity with what below reported, give the compounds of formula VII from which Fosfomycin, that is (1R,2S)-cis-enantiomer of 1,2-epoxypropyl-phosphonic acid, is obtained.

STEP G

The reaction of compound VIII with an aryl or alkylarylsulphonic acid derivative provides the compounds of formula VII in which $R_2$ is aryl or alkylaryl up to 12 carbon atoms. (It is worth noting that the same compounds may also be prepared according to the procedure of steps C and D).

The reaction is carried out in an intert solvent in the presence of a base and at a temperature between $-20°$ C. and 50° C.

Suitable solvents for carrying out the reaction of step G are all the solvents inert with respect to the reactive derivative of the arylsulphonic acid, specific example are methylene chloride, chloroform, acetone, benzene and toluene.

Suitable bases are both inorganic bases such as alkaline carbonates and bicarbonates and tertiary amines such as triethylamine, N-methyl-morpholine and diazabicyclooctane (DABCO).

The reaction temperature is preferably between 0° C. and the room temperature.

The result of this reaction is particularly surprising if it is considered the practically complete chemoselectivity of the acylation that exclusively occurs on the hydroxy in position 1. The high chemoselectivity is still more surprising if it is considered that it appears a peculiar characteristic of the reaction with reactive derivatives of the arylsulphonic acids.

In fact, surprisingly, reactive derivatives of other acids both carboxylic (for example acetyl chloride) and alkylsulphonic (for example methanesulphonyl chloride) afford a mixture of acyl derivatives in position 1 or in position 2 and diacyl derivatives of the compound VIII.

By the process object of the present invention there are obtained the compounds of formula VII having configuration (1R,2S) which is suitable to afford Fosfomycin by epoxide formation.

The reaction may be carried out according to different procedures, see for example British Patent No. 1,266,611 (Merck & Co. Inc.) wherein various reagents and experimental conditions are reported in the formation of 1,2-epoxypropylphosphonic acid starting from derivatives of 1,2-dihydroxypropyl-phosphonic acid.

The preferred epoxidation reaction according to the present invention consists in the treatment of a compound of formula VII with a base in an alcoholic solvent.

Suitable bases are tertiary amines or alkali metal or alkaline earth metal hydroxides or carbonates. Suitable solvents include methanol and ethanol.

The epoxidation may also be conveniently carried out in water in the presence of an alkali metal hydroxide (NaOH or KOH) when in formula VII $R_3$ is hydrogen.

When in the starting compound of formula VII $R_3$ is an alkyl or benzyl radical, the product of the epoxidation reaction is an ester of (1R,2S)-1,2-epoxypropylphosphonic acid, i.e. an ester of Fosfomycin.

The free acid may be easily prepared according to known procedures, for example by treatment with trimethylsilyl chloride and thereafter by hydrolysis.

When in the starting compound of formula VII $R_3$ is a hydrogen radical, that is when compound VII is a free phosphonic acid, the reaction product is a salt of Fosfomycin, (e.g. sodium or potassium salt). When desired, free Fosfomycin may be obtained by treatment with an acid according to known procedures.

The process hereabove discussed provides the intermediates of formula VII for the synthesis of Fosfomycin or a derivative thereof, in a highly enantioselective manner.

The chemical yields of each step are satisfactory, many of them are higher than 90% or quantitative.

The starting product and reagents are inexpensive and easily available and the reaction conditions may easily be industrialized.

As far as we know this is the only industrially suitable process for the preparation of Fosfomycin which does not require a resolution step.

With the aim of better illustrating the invention the following example are given.

EXAMPLE 1

A mixture of aqueous (+)lactic acid at 90% (100 g; 1 mol) acetic acid (690 g), toluene (867 g) and sulphuric acid (11 g) heated up to the boiling temperature by azeotropically separating the water formed during the reaction.

To the mixture cooled at 40°–50° C. sodium acetate (24 g) was added in small portions.

The reaction mixture was cooled at 20° C. and filtered, the solvent was evaporated under vacuum.

2(S)-acetoxypropionic acid (119 g, 0.97 mol, 90% yield) was thereby obtained as oil.

An analitically pure sample was obtained by distillation.

B.p.=85° C./0.3 mmHg.
$[\alpha]_D^{22} = -49.96°$ (C=7.2, chloroform)
$^1$H-NMR (90 MHz, CDCl$_3$-TMS) delta (ppm): 1.50 (d, 3H, J=7 Hz); 2.10 (s, 3H); 5.10 (q, 1H, J=7 Hz); 10.8 (s, 1H).

EXAMPLE 2

A mixture of 2(S)-acetoxypropionic acid (132 g, 1 mol) and thionyl chloride (153 ml; 245 g; 2 mol) was heated at 40° C. for 90 minutes. The reaction mixture was then refluxed heated for 30 minutes and then cooled at 40°–50° C. The excess of thionyl chloride was distilled under vacuum. 2(S)-acetoxypropyl chloride (147.5 g; 0.98 mol, 98% yield) was obtained as oil.

An analitically pure sample was obtained by distillation.

B.p.=20° C./1 mmHg.
$[\alpha]_D^{22} = -35.77°$ (C=7.9, chloroform).
IR (liquid) (cm$^{-1}$): 1820, 1780 (C=0).
$^1$H-NMR (90 MHz, CDCl$_3$-TMS) delta (ppm): 1.63 (d, 1H, J=7 Hz); 2.17 (s, 3H); 5.27 (q, 1H, J=7 Hz).

EXAMPLE 3

Trimethylsilyl-dimethylphosphite (45.27 g; 0.248 mol) was added under nitrogen at 15° C. in 15 minutes to 2(S)-acetoxypropionyl chloride (37.32 g; 0.248 mol). The reaction mixture was kept at 15° C. for 30 minutes then the low-boiling compounds were removed by distillation under vacuum (40°–50° C./10 mmHg). Dimethyl 2(S)-acetoxypropionyl phosphonate (49.95 g) was thereby obtained as oil.

An analitically pure sample was obtained by distillation.

B.p.=109° C./2 mmHg.
$[\alpha]_D^{20} = -25.6°$ (C=1.5, chloroform).
IR (liquid) (cm$^{-1}$): 1750, 1710 (C=0).
$^1$H-NMR (300 MHz, CDCl$_3$-TMS) delta (ppm): 1.52 (d, 3H, J=7.15 Hz); 2.15 (s, 3H); 3.86 (d, 3H, $J_{P\text{-}H}$=11 Hz); 3.90 (d, 3H, $J_{P\text{-}H}$=11 Hz); 5.42 (dq, 1H, $J_{CH_3\text{-}H}$=7.15 Hz, $J_{P\text{-}H}$=0.91 Hz).

EXAMPLE 4

A mixture of di-ter.butylphosphite (2.13 g; 0.11 mol) and hexamethyldisilazane (8.87 g; 0.055 mol) was kept under nitrogen at 100° C. for 2 hours. The mixture was slowly cooled at 15° C. 2(S)-acetoxypropionyl chloride (15.0 g; 0.1 mol) was added under nitrogen at 15° C. in 15 minutes, thereafter the low-boiling compounds were removed by distillation under vacuum (20°–30° C./10 mmHg). Di-ter.butyl 2(S)-acetoxypropionyl phosphonate (27.72 g) was thereby obtained as oil.

IR (liquid) (cm$^{-1}$): 1750, 1715 (C=0).
$^1$H-NMR (300 MHz, CDCl$_3$-TMS) delta (ppm): 1.53 (d, 18H, $J_{P\text{-}H}$=3.45 Hz); 1.55 (d, 3H, J=7 Hz); 2.14 (s, 3H); 5.55 (dq, 1H, $J_{CH_3\text{-}H}$=7 Hz, $J_{P\text{-}H}$=2 Hz).

EXAMPLE 5

To a solution of di-ter.butylphosphite (1.94 g; 10 mmol) in toluene (30 ml) under nitrogen at room temperature triethylamine (1.39 ml; 1.01 g; 10 mmol) and thereafter trimethylsilyl chloride (1.26 ml; 1.082 g; 10 mmol) were added. The reaction mixture was heated up to the reflux temperature for 2 hours and then cooled at 15° C. 2(S)-acetoxypropiolyl chloride (1.43 g; 9.5 mmol) was added at 15° C. in 15 minutes. The reaction mixture was kept at 15° C. for 2 hours, additioned with diethyl ether and filtered, the solvents were evaporated under vacuum. Di-ter-butyl 2(S)-acetoxypropionyl phosphonate (2.63 g) having the same analytical characteristics of the product obtained as described in Example 4, was thereby obtained.

EXAMPLE 6

Tris-trimethylsilylphosphite (5 g; 16.74 mmol) was added under nitrogen at 15° C. in 15 minutes, to 2(S)-acetoxypropionyl chloride (2.52 g; 16.74 mmol). The reaction mixture was kept at 15° C. for 30 minutes then the low-boiling compound were removed by distillation under vacuum (20°–30° C./10 mmHg). Bis-trimethylsilyl 2(S)-acetoxypropionyl phosphonate (5.24 g) was obtained by distillation of the reaction crude.

B.p.=98° C./4 mmHg.

IR (liquid) (cm$^{-1}$): 1750, 1710 (C=O).

$^1$H-NMR (90 MHz, CDCl$_3$-TMS) delta (ppm): 0.27 (s, 18H); 1.63 (d, 3H, J=7 Hz); 2.06 (s, 3H); 5.47 (dq, 1H, J$_{CH_3-H}$=7 Hz, J$_{P-H}$=2 Hz).

EXAMPLE 7

To a solution of bis-trimethylsilyl 2(S)-acetoxypropionyl phosphonate (3.4 g; 10 mmol) in methanol (20 ml), a solution (5.5M) of sodium methoxide in methanol (1.75 ml, 10 mmol) was added unter nitrogen at room temperature.

The solution was kept at room temperature for 30 minutes. Evaporation of the solvent under vacuum affords 2(S)-acetoxypropionyl phosphonic acid monosodium salt (2.14 g).

$^1$H-NMR (300 MHz, D$_2$O-DSS=3-(trimethylsilyl)-propanesulphonic acid sodium salt) delta (ppm): 1.51 (d, 3H, J=7.32 Hz); 2.17 (s, 3H); 5.55 (dq, 1H, J$_{CH_3-H}$=7.32, J$_{P-H}$=1.28 Hz).

EXAMPLE 8

To a solution of (−)-methyl lactate (31.2 g; 0.3 mol) in dichloromethane (300 ml) 4-N,N-dimethylaminopiridine (32.4 g; 0.3 mol) was added. 2,2-Dimethylpropionyl chloride (36.17 g; 0.3 mol) was added under nitrogen at 15° C. to the reaction mixture.

The reaction mixture was kept at 15° C. for 2 hours and filtered. Evaporation of the solvent under vacuum affords methyl 2(S)-(2′,2′-dimethylpropionyloxy)-propanoate (49.63 g) as oil.

$^1$H-NMR (90 MHz, CDCl$_3$-TMS) delta (ppm): 1.20 (s, 9H); 1.48 (d, 3H, J=7 Hz); 3.70 (s, 3H); 5.07 (q, 1H, J=7 Hz).

To a mixture of methyl 2(S)-(2′,2′-dimethylpropionyloxy)-propanoate (44.4 g) and water (50 ml) at 15° C. a solution of sodium hydroxide (9.5 g) in water (18 ml) was added.

The reaction mixture was kept at 15° C. for 2 hours, was acidified at pH 1 by conc. HCl and extracted with diethyl ether (3×50 ml). The reunited organic layers were washed with water and dried on sodium sulphate.

Evaporation of the solvent under vacuum affords 2(S)-(2′,2′-dimethylpropionyloxy)-propionic acid (39 g).

$^1$H-NMR (90 MHz, CDCl$_3$-TMS) delta (ppm): 1.25 (s, 9H); 1.55 (d, 3H, J=7 Hz); 5.10 (q, 1H, J=7 Hz); 10.1 (broad, 1H).

A mixture of 2(S)-(2′,2′-dimethylpropionyloxy)-propionic acid (9.9 g) and thiolyl chloride (14.18 g) was kept at 40° C. for 2 hours and then at reflux temperature for 30 minutes.

The reaction mixture was cooled at 30°–40° C. and the excess thionyl chloride was removed by distillation under vacuum. A residue is thereby obtained which affords by distillation 2(S)-(2′,2′-dimethylpropionyloxy)-propionyl chloride (10.38 g).

B.p.=45° C./1 mmHg.

$^1$H-NMR (90 MHz, CDCl$_3$-TMS) delta (ppm): 1.28 (s, 9H); 1.60 (d, 3H, J=7 Hz); 5.17 (q, 1H, J=7 Hz).

EXAMPLE 9

Trimethylsilyl-dimethylphosphite (2.48 g; 13.6 mmol) was added in 15 minutes at 15° C. and under nitrogen to 2(S)-(2′,2′-dimethylpropionyloxy)-propionyl chloride (2.62 g). The reaction mixture was kept at 15° C. for 1 hour and the low-boiling compounds were removed by evaporation under vacuum. The distillation of the residue affords dimethyl 2(S)-(2′,2′-dimethylpropionyloxy)-propanoyl phosphonate (3.07 g).

B.p.=123° C./3 mmHg.

IR (liquid) (cm$^{-1}$): 1740, 1715 (C=O).

$^1$H-NMR (300 MHz, CDCl$_3$-TMS) delta (ppm): 1.25 (s, 9H); 1.52 (d, 3H, J=7.2 Hz); 3.83 (d, 3H, J$_{P-H}$=11 Hz); 3.85 (d, 3H, J$_{P-H}$=11 Hz); 5.40 (dq, 1H, J$_{CH_3-H}$=7.2 Hz, J$_{P-H}$=2 Hz).

EXAMPLE 10

Tris-trimethylsilylphosphite (2.98 g; 10 mmol) was added in 15 minutes at 15° C. and under nitrogen, to 2(S)-(2′,2′-dimethylpropionyloxy)-propionyl chloride (1.92 g; 10 mmol). The reaction mixture was kept at 15° C. for 1 hour. Evaporation of the low-boiling compounds under vacuum affords bis-trimethylsilyl 2(S)-(2′,2′-dimethylpropionyloxy)-propanoyl phosphonate (3.70 g).

$^1$H-NMR (300 MHz, CDCl$_3$-TMS) delta (ppm): 0.33 (s, 18H); 1.23 (s, 9H); 1.51 (d, 3H, J=7 Hz); 5.50 (dq, 1H, J$_{CH_3-H}$=7 Hz, J$_{P-H}$=2 Hz).

EXAMPLE 11

To a solution of bis-trimethylsilyl 2(S)-(2′,2′-dimethylpropionyloxy)-propanoyl phosphonate (1.91 g; 5 mmol) in methanol (15 ml) a solution of 5.5M of sodium methoxide in methanol (0.875 ml, 5 mmol) was added under nitrogen and at room temperature. The solution was kept at room temperature for 30 minutes. Evaporation of the solvent under vacuum affords the mono sodium salt of 2(S)-(2′,2′-dimethylpropionyloxy)-propanoyl phosphonate (1.23 g).

$^1$H-NMR (300 MHz, D$_2$O-DSS) delta (ppm): 1.25 (s, 9H); 1.55 (d, 3H, J=7 Hz); 5.58 (dq, 1H, J$_{CH_3-H}$=7 Hz, J$_{P-H}$=2 Hz).

EXAMPLE 12

A mixture of di-ter.butylphosphite (0.213 g; 11 mmol) and hexamethyldisilazane (0.887 g; 5.5 mmol) was kept under nitrogen at 100° C. for 2 hours. The mixture was slowly cooled to 15° C.

2(S)-(2′,2′-dimethylpropionyloxy)-propanoyl chloride (1.92 g; 10 mmol) was added under nitrogen at 15° C. in 15 minutes; then the low-boiling compounds were removed by distillation under vacuum (20°–30° C./10 mmHg). Di-ter.butyl 2(S)-(2′,2′-dimethylpropionyloxy)-propanoyl phosphonate (3.25 g) was obtained as oil.

$^1$H-NMR (300 MHz, CDCl$_3$-TMS) delta (ppm): 1.23 (s, 9H); 1.53 (d, 18H, J$_{P-H}$=3.2 Hz); 1.55 (d, 3H, J=7.15 Hz); 5.53 (dq, 1H, J$_{CH_3-H}$=3.67 Hz).

EXAMPLE 13

To a mixture of mono sodium salt of 2(S)-acetoxypropanoyl phosphonic acid (218 mg) in methanol (2 ml) sodium borohydride (9.4 mg; 0.25 mmol) was added in small portions under nitrogen at 20° C. The solution was kept at 20° C. for 15 minutes and the solvent was evaporated under vacuum. Thereby was obtained a mixture of the two diastereoisomers 1(S),2(S) and 1(R),2(S) of the mono sodium salt of 2-acetoxy-1-hydroxypropyl phosphonic acid in the ratio 61:39 respectively.

$^1$H-NMR (300 MHz, D$_2$O-DSS):

Major diastereoisomer: delta (ppm): 1.26 (d, 3H, J=7.2 Hz); 2.03 (s, 3H); 3.86 (dd, 1H, $J_{H-H}$=2.95, $J_{P-H}$=13 Hz); 5.13 (ddq, 1H, $J_{CH3-H}$=7.2 Hz, $J_{H-H}$=2.95 Hz, $J_{P-H}$=6.1 Hz);

Minor diastereoisomer: delta (ppm): 1.26 (d, 3H, J=6.8 Hz); 2.04 (s, 3H); 3.61 (dd, 1H, $J_{H-H}$=5.9 Hz, $J_{P-H}$=10.88 Hz); 5.07 (ddq, 1H, $J_{CH3-H}$=6.8 Hz, $J_{H-H}$=5.9 Hz, $J_{P-H}$=10.8 Hz).

EXAMPLE 14

By carrying out the experiment as described in example 13 and by replacing methanol by water, the mixture of the two diastereoisomers 1(S),2(S) and 1(R),2(S) of the mono sodium salt of 2-acetoxy-1-hydroxypropylphosphonic acid was obtained in the ratio 70:30 respectively.

EXAMPLE 15

By carrying out the experiment as described in example 13 and starting from the mono sodium salt of 2(S)-(2',2'-dimethylpropionyloxy)-propanoyl phosphonic acid a mixture of the two diastereoisomers 1(S),2(S) and 1(R),2(S) of the mono sodium salt of 2-(2',2'-dimethylpropionyloxy)-1-hydroxypropyl phosphonic acid was obtained in the ratio 72:28 respectively.

$^1$H-NMR (300 MHz, D$_2$O-DSS):

Major diastereoisomer: delta (ppm): 1.26 (s, 9H); 1.36 (d, 3H, J=6.41 Hz); 3.96 (dd, 1H, $J_{H-H}$=1.83 Hz, $J_{P-H}$=13.36 Hz); 5.23 (ddq, 1H, $J_{CH3-H}$=6.41 Hz, $J_{H-H}$=1.83 Hz, $J_{P-H}$=5.12 Hz);

Minor diastereoisomer: delta (ppm): 1.28 (s, 9H); 1.36 (d, 3H); 3.73 (dd, 1H, $J_{H-H}$=7.32 Hz, $J_{P-H}$=10.63 Hz); 5.10 (ddq, 1H).

EXAMPLE 16

To a solution of dimethyl 2(S)-(2',2'-dimethylpropionyloxy)-propanoyl phosphonate (5.32 g) in toluene (100 ml), kept at −10° C. under nitrogen, a solution of tetrabutylammonium borohydride (1.29 g; 5 mmol) in toluene (40 ml) was added in 30 minutes.

The reaction mixture was kept at −10° C. for 1 hour, then a solution of acetic acid (0.266 ml) in toluene (50 ml) at −10° C. was added. Evaporation of the solvent under vacuum affords a residue which, after chromatography on silica gel (eluent diethyl ether), affords a mixture of the two diastereoisomers 1(S),2(S) and 1(R),2(S) of dimethyl 2-(2',2'-dimethylpropionyloxy)-1-hydroxypropyl phosphonate in the ratio 80:20 respectively.

$^1$H-NMR (300 MHz, D$_2$O-DSS):

Major diastereoisomer: delta (ppm): 1.19 (s, 9H); 1.30 (dd, 3H, $J_{H-CH3}$=6.78 Hz, $J_{P-H}$=2 Hz); 3.80 (d, 6H, $J_{P-H}$=10.62 Hz); 4.24 (dd, 1H, $J_{H-H}$=2.93 Hz, $J_{P-H}$=12.45 Hz); 5.20 (ddq, 1H, $J_{CH3-H}$=6.78 Hz, $J_{H-H}$=2.93 Hz, $J_{P-H}$=6.78 Hz);

Minor diastereoisomer: delta (ppm) (meaningful resonances): 1.18 (s, 9H); 1.33 (d, 3H, J=6.78 Hz); 4.26 (dd, 1H, $J_{H-H}$=4.68 Hz, $J_{P-H}$=10.55 Hz); 5.11 (ddq, 1H).

Crystallization of the mixture from ethyl ether-hexane affords the pure 1(S),2(S) diastereoisomer.

EXAMPLE 17

By carrying out the experiment as described in example 16, at the temperature of −70° C. a mixture of the two diastereoisomers 1(S),2(S) and 1(R),2(S) of dimethyl 2-(2',2'-dimethylpropionyloxy)-1-hydroxypropyl phosphonate was obtained in the ratio 88:12 respectively.

EXAMPLE 18

By carrying out the experiment as described in example 16, by using tetrahydrofuran instead of toluene, a mixture of the two diastereoisomers of 1(S),2(S) and 1(R),2(S) of dimethyl 2-(2',2'-dimethylpropionyloxy)-1-hydroxypropyl phosphonate was obtained in the ratio 86:14 respectively.

EXAMPLE 19

By carrying out the experiment as described in example 16 and starting from dimethyl 2(S)-acetoxypropanoyl phosphonate a mixture of the two diastereoisomers 1(S),2(S) and 1(R),2(S) of dimethyl 2-acetoxy-1-hydroxypropyl phosphate was obtained in the ratio 75:25.

$^1$H-NMR (300 MHz, CDCl$_3$-TMS):

Major diastereoisomer: delta (ppm): 1.37 (dd, 3H, $J_{H-CH3}$=6.41 Hz, $J_{P-H}$=0.91 Hz); 2.09 (s, 3H); 3.26 (dd, OH, 1H, $J_{H-OH}$=8.60 Hz, $J_{P-H}$=5.67 Hz); 3.80 (d, 3H, $J_{P-H}$=10.8 Hz); 3.81 (d, 3H, $J_{P-H}$=10.8 Hz); 3.87 (ddd, 1H, $J_{H-H}$=4.07 Hz, $J_{OH-H}$=8.60 Hz, $J_{P-H}$=10.62 Hz); 5.26 (ddq, 1H, $J_{H-H}$=4.07 Hz, $J_{CH3-H}$=6.41 Hz, $J_{P-H}$=0.73 Hz).

EXAMPLE 20

To a solution of di-ter.butyl 2(S)-acetoxypropanoyl phosphonate (3.08 g) and trimethylborate (0.052 g; 0.5 mmol) in diethyl ether (50 ml), kept at −10° C. under nitrogen, sodium borohydride (0.380 g; 10 mmol) was added.

The reaction mixture was kept at −10° C. for 20 hours. The reaction mixture was warmed at 20° C. and washed with a sodium chloride saturated solution and the organic solvent dried on sodium sulphate.

Evaporation of the solvent under vacuum affords a mixture of the two diastereoisomers 1(S),2(S) and 1(R),2(S) of di-ter.butyl 2-acetoxy-1-hydroxypropyl phosphonate in the ratio 73:27 respectively.

$^1$H-NMR (300 MHz, CDCl$_3$-TMS):

Major diastereoisomer: delta (ppm): 1.35 (dd, 3H, $J_{H-CH3}$=6.23 Hz, $J_{P-H}$=2 Hz); 1.50 (tBu, 18H); 2.06 (s, 3H); 2.83 (dd, OH, 1H, $J_{H-HO}$=7.4 Hz, $J_{P-OH}$=7.4 Hz); 3.62 (ddd, 1H, $J_{H-H}$=4.58 Hz, $J_{OH-H}$=7.4 Hz, $J_{P-H}$=10.44 Hz); 5.17 (ddq, 1H, $J_{H-H}$=4.58 Hz, $J_{CH3-H}$=6.23 Hz, $J_{P-H}$=8.61 Hz);

Minor diastereoisomer: delta (ppm): 1.35 (d, 3H, J=6.2 Hz); 1.50 (tBu, 18H); 2.07 (s, 3H); 3.10 (dd, OH, 1H, $J_{H-HO}$=5.8 Hz, $J_{P-OH}$=9.96 Hz); 3.86 (ddd, 1H, $J_{H-H}$=3.85 Hz, $J_{P-H}$=8.61 Hz, $J_{OH-H}$=9.96 Hz); 5.17 (m, 1H).

EXAMPLE 21

To a solution of di-ter.butyl 2(S)-acetoxypropanoyl phosphonate (3.08 g) in toluene (50 ml), kept at 20° C. under nitrogen, tetrabutylammonium bromide (161 mg, 0.5 mmol) and sodium borohydride (378 mg, 10 mmol) were consecutively added.

The reaction mixture was kept at 20° C. for 18 hours. The reaction mixture was worked up as described in example 22. A mixture of the two diastereoisomers 1(S),2(S) e 1(R),2(S) of di-ter.butyl 2-acetoxy-1-hydroxypropyl phosphonate was then obtained in the ratio 70:30.

EXAMPLE 22

To a solution of dimethyl (1S,2S)-2-(2',2'-dimethylpropionyloxy)-1-hydroxypropyl phosphonate (2.68 g) in dichloromethane (1.5 ml), under nitrogen at room temperature, pyridine (0.95 g; 12 mmol) was added. To the solution cooled at 0° C. a solution of methanesulphonyl chloride (1.59 g; 11 mmol) in dichloromethane (1.5 ml) was added, under nitrogen.

The reaction mixture was kept at 0° C. for 16 hours, poured in a mixture of diluted HCl and ice, extracted with dichloromethane (3×10 ml).

The reunited organic layers were washed with a sodium chloride saturated solution and dried on sodium sulphate. Evaporation of the solvent under vacuum affords dimethyl (1S,2S)-2-(2',2'-dimethylpropionyloxy)-1-methanesulphonyloxypropyl phosphonate (3.40 g).

$^1$H-NMR (300 MHz, CDCl$_3$-TMS) delta (ppm): 1.21 (s, 9H); 1.36 (d, 3H, J=6.41 Hz); 3.23 (s, 3H); 3.84 (d, 3H, J$_{P-H}$=11.20 Hz); 3.86 (d, 3H, J$_{P-H}$=11.20 Hz); 4.93 (dd, 1H, J$_{H-H}$=5.68 Hz, J$_{P-H}$=11.36 Hz); 5.28 (ddq, 1H, J$_{H-H}$=5.68 Hz, J$_{CH3-H}$=6.41 Hz, J$_{P-H}$=1.1 Hz).

EXAMPLE 23

By carrying out the experiment as described in example 22, starting from dimethyl (1S,2S)-2-acetoxy-1-hydroxypropyl phosphonate, the dimethyl (1S,2S)-2-acetoxy-1-methanesulphonyloxy-propyl phosphonate was obtained.

$^1$H-NMR (300 MHz, CDCl$_3$-TMS) delta (ppm): 1.39 (d, 3H, J=6.8 Hz); 2.09 (s, 3H); 3.20 (s, 3H); 3.84 (d, 3H, J$_{P-H}$=10.7 Hz); 3.86 3H, J$_{P-H}$=10.7 Hz); 4.88 (dd, 1H, J$_{H-H}$=5.8 Hz, J$_{P-H}$=11.2 Hz); 5.36 (ddq, 1H, J$_{CH3-H}$=6.8 Hz, J$_{H-H}$=5.8 Hz, J$_{P-H}$=1.2 Hz).

EXAMPLE 24

A solution of dimethyl (1S,2S)-2-acetoxy-1-methanesulphonyloxypropyl phosphonate (3.04 g) and methanesulphonic acid (0.960 g; 10 mmol) in methanol (60 ml) was kept at the reflux temperature for 6 hours.

The reaction mixture was cooled at 20° C. and neutralized with sodium methoxide (0.640 g; 10 mmol).

Evaporation of the solvent under vacum affords a residue which was recovered by acetone and filtered. Evaporation of the solvent under vacuum affords dimethyl (1S,2S)-2-hydroxy-1-methanesulphonyloxypropyl phosphonate (2.52 g).

$^1$H-NMR (300 MHz, CDCl$_3$-TMS) delta (ppm): 1.38 (dd, 3H, J$_{H-CH3}$=6.2 Hz, J$_{P-H}$=0.6 Hz); 3.19 (s, 3H); 3.86 (d, 3H, J$_{P-H}$=10.4 Hz); 3.88 (d, 3H, J$_{P-H}$=10.4 Hz); 4.30 (ddq, 1H, J$_{CH3-H}$=6,2 Hz, J$_{H-H}$=3.84 Hz, J$_{P-H}$=4.4 Hz); 4.85 (dd, 1H, J$_{H-H}$=3.84 Hz, J$_{P-H}$=10.6 Hz).

EXAMPLE 25

To a solution of dimethyl (1S,2S)-2-hydroxy-1-methanesulphonyloxypropyl phosphonate (2.52 g) in methanol (25 ml), at 15° C., potassium carbonate (1.38 g; 10 mmol) was added. The reaction mixture was kept at 15° C. for 4 hours and filtered on celite.

Evaporation of the solvent under vacuum affords a residue which was recovered by acetone (20 ml).

The insoluble was filtered and the evaporation of the solvent afforded dimethyl (1R,2S)-1,2-epoxypropyl phosphonate.

$^1$H-NMR (300 MHz, CDCl$_3$-TMS) delta (ppm): 1.56 (dd, 3H, J$_{H-CH3}$=5.86 Hz, J$_{P-CH3}$=0.7 Hz); 2.96 (dd, 1H, J$_{H-H}$=4.4 Hz, J$_{P-H}$=27.5 Hz); 3.30 (ddq, 1H, J$_{H-H}$=4.4 Hz, J$_{CH3-H}$=5.86 Hz, J$_{P-H}$=11 Hz); 3.79 (d, 3H, J$_{P-H}$=11.2 Hz); 3.82 (d, 3H, J$_{P-H}$=11.2 Hz).

The optical purity was confirmed by the $^1$H-NMR (300 MHz) analysis carried out in CDCl$_3$ using the optically active shift reagent Eu(tfc)$_3$ Europium (III) tris[3-(trifluoromethyl-hydroxymethylene)-d-camphorate].

EXAMPLE 26

By carrying out the experiment as described in example 22, starting from di-ter.butyl (1S,2S)-2-acetoxy-1-hydroxypropyl phosphonate, di-ter.butil (1S,2S)-2-acetoxy-1-methanesulphonyloxypropyl phosphonate was obtained.

$^1$H-NMR (300 MHz, CDCl$_3$-TMS) delta (ppm): 1.36 (d, 3H, J=6.8 Hz); 1.54 (tBu, 18H); 2.10 (s, 3H); 3.23 (s, 3H); 4.66 (dd, 1H, J$_{H-H}$=7.5 Hz, J$_{P-H}$=10 Hz); 5.24 (ddq, 1H, J$_{CH3-H}$=6.8 Hz, J$_{H-H}$=7.5 Hz, J$_{P-H}$=1.2 Hz).

EXAMPLE 27

A solution of di-ter.butyl (1S,2S)-2-acetoxy-1-methanesulphonyloxypropyl phosphonate (3.87 g) and methanesulphonic acid (9.6 mg) in methanol (60 ml) was kept at the reflux temperature for 6 hours. Evaporation of the solvent under vacuum affords (1S,2S)-2-hydroxy-1-methanesulphonyloxypropyl phosphonic acid.

$^1$H-NMR (300 MHz, D$_2$O-DSS): delta (ppm): 1.25 (d, 3H, J=6.6 Hz); 3.20 (s, 3H); 4.12 (ddq, 1H, J$_{H-H}$=5.4 Hz, J$_{CH3-H}$=6.6 Hz); 4.65 (dd, 1H, J$_{H-H}$=5.4 Hz, J$_{P-H}$=10.3 Hz).

EXAMPLE 28

To a solution of (1S,2S)-2-hydroxy-1-methanesulphonyloxypropyl phosphonic acid (2.34 g) in methanol (10 ml) a 5.55M solution of sodium methoxide in methanol (3.6 ml; 20 mmol) was added at 15° C. under nitrogen. The reaction mixture was kept at 15° C. for 15 minutes.

Evaporation of the solvent under vacuum affords disodium (1S,2S)-2-hydroxy-1-methanesulphonyloxypropyl phosphonate (2.78 g).

$^1$H-NMR (300 MHz, D$_2$O-DSS): delta (ppm): 1.34 (d, 3H, J=6.78 Hz); 3.30 (s, 3H); 4.18 (ddq, 1H, J$_{CH3-H}$=6.78 Hz, J$_{H-H}$=5.13 Hz, J$_{P-H}$=3.66 Hz); 4.56 (dd, 1H, J$_{H-H}$=5.13 Hz, J$_{P-H}$=9.53 Hz).

EXAMPLE 29

To a solution of disodium (1S,2S)-2-hydroxy-1-methanesulphonyloxypropyl phosphonate (2.78 g) in water (10 ml) an aqueous solution 1N of sodium hydroxide (10 ml, 10 mmol) was added at 15° C. The reaction mixture was kept at 15° C. for 2 hours. Evaporation of the solvent affords disodium (1R,2S)-1,2-epoxypropyl phosphonate.

$^1$H-NMR (300 MHz, D$_2$O-DSS): delta (ppm): 1.50 (d, 3H, J=6 Hz); 2.83 (dd, 1H, J$_{H-H}$=5.4 Hz, J$_{P-H}$=18 Hz); 3.27 (ddq; 1H, J$_{CH3-H}$=6 Hz, J$_{H-H}$=5.4 Hz).

EXAMPLE 30

To a solution of dimethyl (1S,2S)-2-acetoxy-1-hydroxypropyl phosphonate (22.6 g; 0.1 mol) in methanol (500 ml) methanesulphonic acid (9.6 g; 0.1 mol) was added.

The solution was kept at the reflux temperature for 10 hours, cooled at 15° C., neutralized by potassium carbonate (1.38 g; 0.1 mol) and filtered.

Evaporation of the solvent under vacuum affords the dimethyl (1S,2S)-1,2-dihydroxypropyl phosphonate (16.5 g; 0.09 mol; 90% yield).

$^1$H-NMR (300 MHz, CDCl$_3$-TMS): delta (ppm): 1.30 (dd, 3H, $J_{H\text{-}CH_3}=6.4$ Hz, $J_{P\text{-}H}=1.8$ Hz); 3.74 (dd, 1H, $J_{H\text{-}H}=3.1$ Hz, $J_{P\text{-}H}=8$ Hz); 3.80 (d, 3H, $J_{P\text{-}OCH_3}=10.5$ Hz); 3.85 (d, 3H, $J_{P\text{-}OCH_3}=10.5$ Hz); 4.15 (ddq, 1H, $J_{CH_3\text{-}H}=6.4$ Hz, $J_{H\text{-}H}=3.1$ Hz, $J_{P\text{-}H}=4.6$ Hz).

EXAMPLE 31

A solution of dimethyl (1S,2R)-1,2-epoxypropyl phosphonate (18.4 g; 0.1 mol) in water (200 ml) was kept at 100° C. for 3 hours. The solution was cooled at 20° C. and the solvent evaporated under vacuum.

The dimethyl (1S,2S)-1,2-dihydroxypropyl phosphonate was thus obtained.

EXAMPLE 32

To a solution of dimethyl (1S,2S)-1,2-dihydroxypropyl phosphonate (1.84 g; 10 mmol) in dichloromethane (20 ml), kept at 15° C. under stirring, potassium carbonate (2.72 g; 20 mmol) and then p-toluenesulphonyl chloride (1.90 g; 10 mmol) were added.

The reaction mixture was kept at 15° C. for 24 hours, diluted with acetone (20 ml), filtered and the filtrate concentrated under vacuum. A crude was thus obtained which, after purification by chromatography on silica gel (eluent diethylether:ethylacetate=8:2), afforded dimethyl (1S,2S)-2-hydroxy-1-p-toluenesulphonyloxypropyl phosphonate (3.04 g; 9 mmol; 90% yield).

M.p.=68°-70° C.

$[\alpha]_{365}^{20}=+48.8°$ (c=1, chloroform).

$^1$H-NMR (300 MHz, CDCl$_3$-TMS) delta (ppm): 1.24 (dd, 3H, J=6.23 Hz); 2.88 (d, 1H, J=6.8 Hz); 3.67 (d, 3H, J=10.8 Hz); 3.73 (d, 3H, J=10.8 Hz); 4.15 (dddq, 1H, J=6.23 Hz, $J_{H\text{-}H}=3.8$ Hz, $J_{P\text{-}H}=10.2$ Hz, $J_{OH\text{-}H}=6.8$ Hz); 4.77 (dd, 1H, $J_{H\text{-}H}=3.8$ Hz, $J_{P\text{-}H}=10.8$ Hz); 7.30-8.20 (AA'BB', 4H, aromatic protons).

EXAMPLE 33

To a solution of dimethyl (1S,2S)-2-hydroxy-1-p-toluenesulphonyloxypropyl phosphonate (1.69 g; 5 mmol) in methanol (50 ml), kept at 15° C. under stirring, potassium carbonate (1.03 g; 7.5 mmol) was added.

The reaction mixture was kept at 15° C. for 3 hours and concentrated under vacuum.

The crude was recovered with acetone (30 ml), filtered and the filtrate concentrated under vacuum.

Dimethyl (1R,2S)-1,2-epoxypropyl phosphonate (0.789 g; 4.75 mmol, 95% yield) was thus obtained.

$[\alpha]_{436}^{20}=+7.2°$ (c=1, chloroform).

$^1$H-NMR (300 MHz, CDCl$_3$-TMS) delta (ppm): 1.56 (dd, 3H, $J_{H\text{-}CH_3}=5.86$ Hz, $J_{P\text{-}CH_3}=0.7$ Hz); 2.96 (dd, 1H, $J_{H\text{-}H}=4.4$ Hz, $J_{P\text{-}H}=27.5$ Hz); 3.30 (ddq, 1H, $J_{H\text{-}H}=4.4$ Hz, $J_{CH_3\text{-}H}=5.86$ Hz, $J_{P\text{-}H}=11$ Hz); 3.79 (d, 3H, $J_{P\text{-}OCH_3}=5.3$ Hz); 3.82 (d, 3H, $J_{P\text{-}OCH_3}=5.3$ Hz).

On the basis of the $^1$H-NMR (300 MHz, CDCl$_3$) analysis carried out using the optically active shift reagent Eu(tfc)$_3$ the product was enantiomerically pure.

EXAMPLE 34

To a solution of dimethyl (1S,2S)-2-hydroxy-1-p-toluenesulphonyloxypropyl phosphonate (1.69 g; 5 mmol) in chloroform (5 ml), at 20° C. under stirring, trimethylsilylbromide (2.3 g; 15 mmol) was added.

The reaction mixture was kept at 20° C. for 4 hours. Evaporation of the solvent under vacum affords the crude bis-trimethylsilyl (1S,2S)-2-hydroxy-1-p-toluenesulphonyloxypropyl phosphonate which was added with methanol (50 ml).

The methanolic solution was kept at room temperature for 2 hours. Evaporation of the solvent under vacuum afforded (1S,2S)-2-hydroxy-1-p-toluenesulphonyloxypropyl phosphonic acid (1.47 g; 0.047 mmol; 95% yield).

$^1$H-NMR (300 MHz, D$_2$O-DSS) delta (ppm): 1.15 (d, 3H, J=6.4 Hz); 2.41 (s, 3H); 4.07 (dq, 1H, $J_{H\text{-}H}=5.7$ Hz, $J_{CH_3\text{-}H}=6.4$ Hz); 4.64 (dd, 1H, $J_{H\text{-}H}=5.7$ Hz, $J_{P\text{-}H}=10.25$ Hz); 7.4-7.85 (AA'BB', 4H, aromatic protons).

EXAMPLE 35

To a solution of (1S,2S)-2-hydroxy-1-p-toluenesulphonyloxypropyl phosphonic acid (1.47 g; 0.047 mmol) in methanol (20 ml) at 15° C. and under nitrogen, sodium methoxide (0.81 g; 15 mmol) was added. The reaction mixture was kept at 15° C. for 4 hours, filtered and diluted with isopropanol (20 ml).

The precipitate was filtered, washed with isopropanol and dried. The disodium (1R,2S)-cis-1,2-epoxypropyl phosphonate (0.76 g; 0.042 mmol, 89% yield) was thus obtained.

$[\alpha]_D^{20}=-18.8°$ (c=10, water).

$^1$H-NMR (300 MHz, D$_2$O-DSS) delta (ppm): 1.50 (d, 3H, J=6 Hz); 2.83 (dd, 1H, $J_{H\text{-}H}=5.4$ Hz, $J_{P\text{-}H}=18$ Hz); 3.27 (ddq, 1H, $J_{CH_3\text{-}H}=6$ Hz, $J_{H\text{-}H}=5.4$ Hz).

EXAMPLE 36

By carrying out the experiment as described in example 3 by using acetone instead of dichloromethane the dimethyl (1S,2S)-2-hydroxy-1-p-toluenesulphonyloxypropyl phosphonate was obtained in 80% yield.

EXAMPLE 37

By carrying out the experiment as described in example 3 by using benzenesulphonyl chloride instead of p-toluenesulphonyl chloride the dimethyl (1S,2S)-2-hydroxy-1-benzenesulphonyloxypropyl phosphonate was obtained.

$^1$H-NMR (300 MHz, CDCl$_3$O-TMS): delta (ppm): 1.28 (d, 3H, J=6.8 Hz); 2.90 (d, 1H, J=6.8 Hz); 3.66 (d, 3H, $J_{P\text{-}H}=10.8$ Hz); 3.72 (d, 3H, $J_{P\text{-}H}=10.8$ Hz); 4.19 (dddq, 1H, J=6.8 Hz, $J_{OH\text{-}H}=6.8$ Hz, $J_{H\text{-}H}=4$ Hz, $J_{P\text{-}H}=10$ Hz); 4.81 (dd; 1H, $J_{H\text{-}H}=4$ Hz, $J_{P\text{-}H}=11$ Hz); 7.55-8.00 (m, 5H, aromatic protons).

EXAMPLE 38

By carrying out the experiment as described in example 3 by using 1-naphthylsulphonyl chloride instead of p-toluenesulphonyl chloride the dimethyl (1S,2S)-2-hydroxy-1-(1-naphthylsulphonyloxy)-propyl phosphonate was obtained.

$^1$H-NMR (300 MHz, acetone-d$_6$-TMS): delta (ppm): 1.21 (d, 3H, J=6.1 Hz); 2.83 (d, 1H, J=7 Hz); 3.27 (d, 3H, $J_{P\text{-}H}=11$ Hz); 3.47 (d, 3H, $J_{P\text{-}H}=11$ Hz); 4.12 (dddq, 1H, J=6.1 Hz, $J_{H\text{-}H}=3.7$ Hz, $J_{OH\text{-}H}=7$ Hz, $J_{P-H}=9.8$ Hz); 4.81 (dd, 1H, $J_{H-H}=4.7$ Hz, $J_{P-H}=10.8$ Hz); 7.65–8.70 (m, 9H, aromatic protons).

What we claim is:

1. A enantioselective process for the preparation of (1S,2S)-1,2-dihydroxypropyl-phosphonic acid derivatives of formula

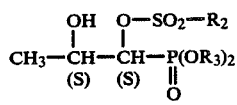   (VII)

wherein $R_2$ represents aryl or alkylaryl having up to 12 carbon atoms, the substituents $R_3$, independently, represent hydrogen or sodium, lower alkyl or benzyl;

said process comprising (A) the reaction of an O-acylated derivative of lactic acid of formula

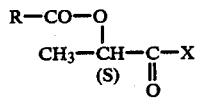   (II)

wherein

R represents lower alkyl, lower alkoxy, an optionally substituted phenyl, benzyl or naphthyl, X is a chlorine or bromine atom, lower alkoxy, lower alkylsulphonyloxy or lower alkoxycarbonyloxy group;

with a trimethylsilyl-dialkyl-phosphite of formula $(CH_3)_3Si-O-P(OR_1)_2$ (III)

wherein the $R_1$'s, equal to or different from each other, represent lower alkyl, benzyl or trimethylsilyl, to obtain a propionyl-phosphonate of formula

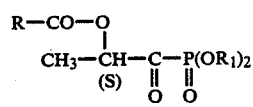   (IV)

wherein R and $R_1$ have the above meanings;

(B) the reduction of compound IV by a borohydride or an aluminum-hydride in an aprotic solvent to obtain the compound of formula

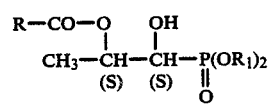   (V)

wherein R and $R_1$ have the above meanings;

(E) the deprotection of the hydroxy group in position 2 of compound V by reaction with water or alcohol in the presence of a strong acid to obtain a compound of formula

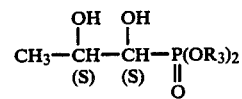   (VIII)

wherein the $R_3$'s have the above meanings; and (G) the reaction of compound VIII with a reactive derivative of an aryl or alkylarylsulphonic acid having up to 12 carbon atoms in an inert solvent, in the presence of a base and at $-20°$ and $50°$ C., to obtain compounds VII in which $R_2$ is aryl or alkylaryl of up to 12 carbon atoms.

2. An enantioselective process according to claim 1, wherein the reaction of step A is carried out in the absence of solvents and catalysts.

3. An enantioselective process according to claim 1, wherein in step A the compound of formula III is prepared in situ from a silylating agent and a dialkylphosphite.

4. An enantioselective process according to claim 1, wherein the borohydride used in step B is sodium or tetraalkylammonium borohydride.

5. A process according to claim 1, wherein in the compounds of formula VII obtained by step G, $R_2$ is selected from the class consisting of phenyl, tolyl, 1- and 2-naphthyl.

* * * * *